(12) United States Patent
Dubin et al.

(10) Patent No.: US 10,035,147 B2
(45) Date of Patent: *Jul. 31, 2018

(54) WAFER WITH GEL-BASED BIOCHIPS FOR ELECTROCHEMICAL SYNTHESIS AND ELECTRICAL DETECTION OF POLYMERS

(71) Applicant: Intel Corporation, Santa Clara, CA (US)

(72) Inventors: Valery M. Dubin, Portland, OR (US); Nikolay Suetin, Moscow (RU)

(73) Assignee: Intel Corporation, Santa Clara, CA (US)

( * ) Notice: Subject to any disclaimer, the term of this patent is extended or adjusted under 35 U.S.C. 154(b) by 74 days.

This patent is subject to a terminal disclaimer.

(21) Appl. No.: 14/587,304

(22) Filed: Dec. 31, 2014

(65) Prior Publication Data

US 2015/0231633 A1     Aug. 20, 2015

Related U.S. Application Data

(62) Division of application No. 11/771,536, filed on Jun. 29, 2007, now Pat. No. 8,940,143.

(51) Int. Cl.
| | |
|---|---|
| *G01N 27/26* | (2006.01) |
| *G01N 33/543* | (2006.01) |
| *B01J 19/00* | (2006.01) |
| *B01L 3/00* | (2006.01) |
| *G01N 27/327* | (2006.01) |

(52) U.S. Cl.
CPC .... *B01L 3/502715* (2013.01); *G01N 27/3277* (2013.01); *B01J 2219/00644* (2013.01); *B01L 2300/0645* (2013.01); *G01N 33/5436* (2013.01)

(58) Field of Classification Search
None
See application file for complete search history.

(56) References Cited

U.S. PATENT DOCUMENTS

| | | |
|---|---|---|
| 5,352,574 A | 10/1994 | Guiseppi-Elie |
| 5,445,934 A | 8/1995 | Fodor et al. |
| 5,552,270 A | 9/1996 | Khrapko et al. |

(Continued)

FOREIGN PATENT DOCUMENTS

| | | |
|---|---|---|
| DE | 10233212 | 2/2004 |
| FR | 2781886 | 2/2000 |

(Continued)

OTHER PUBLICATIONS

Rubina, A. Y. et al., "Hydrogel-Based Protein Microchips: Manufacturing, Properties, and Applications," Bio Techniques 34:1008-1022, May 2003.

(Continued)

*Primary Examiner* — Yelena G Gakh
*Assistant Examiner* — Michelle Adams
(74) *Attorney, Agent, or Firm* — Schwegman Lundberg & Woessner, P.A.

(57) ABSTRACT

An embodiment of the invention relates to a wafer comprising a plurality of biochips and interconnects on the wafer, the biochip comprising a biochip pad, a synthesis electrode and a gel comprising a probe, wherein a plurality of the biochip pads of the plurality of the biochips are interconnected by the interconnects to carry out a chemical reaction on a plurality of the synthesis electrodes.

11 Claims, 8 Drawing Sheets

(56) References Cited

U.S. PATENT DOCUMENTS

| | | | |
|---|---|---|---|
| 5,653,930 A | 8/1997 | Noda et al. | |
| 5,653,939 A * | 8/1997 | Hollis | B01J 19/0046 |
| | | | 204/456 |
| 5,766,934 A | 6/1998 | Guiseppi-Elie | |
| 5,874,219 A | 2/1999 | Rava et al. | |
| 6,093,302 A | 7/2000 | Montgomery | |
| 6,121,048 A | 9/2000 | Zaffaroni et al. | |
| 6,251,595 B1 | 6/2001 | Gordon et al. | |
| 6,280,595 B1 | 8/2001 | Montgomery | |
| 6,444,111 B1 | 9/2002 | Montgomery | |
| 6,456,942 B1 | 9/2002 | Anderson | |
| 6,566,495 B1 | 5/2003 | Fodor et al. | |
| 6,602,400 B1 | 8/2003 | Choong et al. | |
| 6,838,053 B2 | 1/2005 | John et al. | |
| 7,208,077 B1 | 4/2007 | Albers et al. | |
| 8,940,143 B2 * | 1/2015 | Dubin | B01J 19/0046 |
| | | | 204/400 |
| 2003/0059929 A1 | 3/2003 | Heller et al. | |
| 2004/0105207 A1 * | 6/2004 | Spaderna | H01L 27/118 |
| | | | 361/115 |
| 2006/0024813 A1 | 2/2006 | Warthoe | |
| 2006/0275927 A1 | 12/2006 | Dublin et al. | |

FOREIGN PATENT DOCUMENTS

| | | |
|---|---|---|
| WO | 9322678 | 11/1993 |
| WO | 9967019 | 12/1999 |
| WO | 0051721 | 9/2000 |
| WO | 0062048 | 10/2000 |
| WO | 0183674 | 11/2001 |
| WO | 0231463 | 4/2002 |
| WO | 2005075995 | 8/2005 |
| WO | 2005095963 | 10/2005 |
| WO | 2006133042 | 12/2006 |

OTHER PUBLICATIONS

Jain et al., "Porous sillica materials as low-k dielectrics for electronic and optical interconnects," Thin Solid Filsrn 398-399, 2001, 513-522.

* cited by examiner

BASE = protected A or T or G or C

WAFER WITH GEL-BASED BIOCHIPS FOR ELECTROCHEMICAL SYNTHESIS AND ELECTRICAL DETECTION OF POLYMERS

CROSS-REFERENCE RELATED APPLICATIONS

This application is a divisional application of U.S. application Ser. No. 11/771,536, filed Jun. 29, 2007, and is now allowed. This application is related to U.S. application Ser. No. 11/144,679, filed on Jun. 6, 2005. The disclosures of the prior application are considered part of and are incorporated herein in its entirety by reference.

FIELD OF INVENTION

The embodiments of the invention relate to electrochemical synthesis and electrical detection of a polymer with a gel-based biochip, and it relates to methods and apparatus for preparing such arrays. The invention transcends several scientific disciplines such as polymer chemistry, biochemistry, molecular biology, medicine and medical diagnostics.

BACKGROUND

Synthesis of high density polymer arrays on a microarray chip is known. Examples of such high density polymer arrays include nucleic acid arrays, peptide arrays, and carbohydrate arrays.

One method of preparing polymer arrays on microarray chips involves photolithographic techniques using photocleavable protecting groups (FIG. 1). For example, the method includes attaching photoreactive groups to the surface of a substrate, exposing selected regions of the substrate to light to activate those regions, attaching a monomer with a photoremovable group to the activated regions, and repeating the steps of activation and attachment until macromolecules of the desired length and sequence are synthesized. However, the devices made by the photolithographic methods are not scalable to sub 1 um features due to the limitation in synthesis and optical detection. Typically molecular recognition events are detected through optical readout of fluorescent labels attached to target molecules specifically bound to the probe molecules. Thus, the detection of molecular recognition events is difficult to implement and miniaturize, relies on the use of optical labels, and requires large or expensive instrumentation.

Additional methods and techniques applicable to polymer array synthesis include electrochemical synthesis. One example includes providing a porous substrate with an electrode therein, placing a molecule having a protected chemical group in proximity of the porous substrate, placing a buffering solution in contact with the electrode and the porous substrate to prevent electrochemically generated reagents from leaving the locality of the electrode (the use of confinement electrodes to prevent reagents from diffusing away have also been described), applying a potential to the electrode to generate electrochemical reagents capable of deprotecting the protected chemical functional group of the molecule, attaching the deprotected chemical functional group to the porous substrate or a molecule on the substrate, and repeating the above steps until polymers of the desired length and sequence are synthesized.

One manufacturer produces devices with electrochemical synthesis on planar Pt electrodes and optical detection. Scalability and sensitivity of these devices are poor. Enzymatic current is measured on the electrode arrays. However, this technique does not have on-die amplification. The device density is also low (1K or 12K electrodes) and current measurements are limited in sensitivity to pA ranges.

High-density DNA microarray chips have been useful tools for probing deep and wide-ranging questions in biology, but they can't track protein activities. Although DNA chips can be fabricated and stored dry for long periods of time, the formation of high-density protein chips to fully understand protein functions has so far been a tremendous challenge. This is because proteins need to be in a wet environment in order to remain structurally intact and carry out their biological functions. Despite the serious effort and progress made in fabrication techniques, this requirement is still a barrier to the development and use of suitable protein chips. The embodiments of the invention overcome this barrier.

BRIEF DESCRIPTION OF THE DRAWINGS

FIG. 4(a) shows the layout of a wafer with pads on the biochips (DP1, DP2, DP3) interconnected across the scribe lines to the contact pads on the wafer (WP1, WP2, WP3). FIG. 4(b) shows a portion of electrode array on a die called an element, pad, or spot containing anode, working and confinement electrodes.

DETAILED DESCRIPTION

Figure 1:
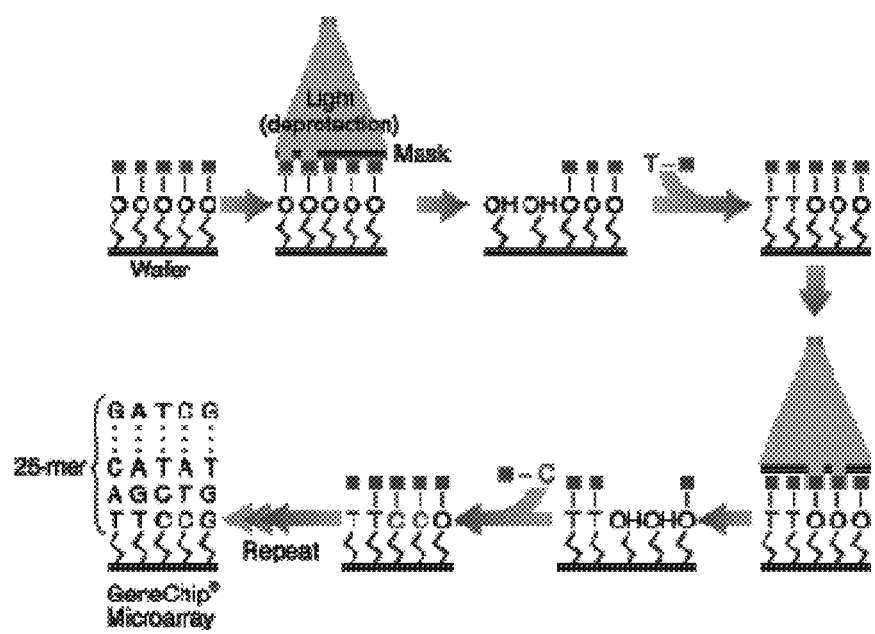
FIG. 1 shows the present state of the art biochip on a planar surface. This biochip was made using a combination of photolithography and combinatorial chemistry.

The embodiments of the invention address the some of the problems present in present state of the art biochips, namely: (1) Low sensitivity of electrical detection on a surface of the biochip due to low coverage of polymers. (2) Limited scalability for devices based on the electrical detection of binding events on planar surface because decreasing surface area will decrease the sensitivity due to lower surface concentration of chemical probes/targets on a planar two-dimensional surface. (3) Low stability for polymers attached to planar surfaces due to non-covalent bonding. (4) High cost of bio chips for biochips synthesized by optical lithography. (5) Fabrication of hand held devices for medical diagnostics is difficult for fluorescence detection using optical scanners—as explained above, the present state of the art biochips detect molecular recognition events through optical readout of fluorescent labels. (6) Lack of label free detection of binding events. (7) Protein array fabrication is difficult since proteins need to be kept wet to maintain their structures.

The rest of the Detailed Description describes how the above mentioned problems addressed by the embodiments of the invention have been.

Nucleic acids (DNA and RNA) can form double-stranded molecules by hybridization, that is, complementary base pairing. The specificity of nucleic acid hybridization is such that a particular DNA or RNA molecule can be labeled (e.g., with a radioactive or fluorescent tag) to generate a probe, and be used to isolate a complementary molecule (target)

from a very complex mixture, such as a whole genomic DNA or whole cellular RNA. It is also possible to label the target instead of labeling the probe or label both the probe and the target. This specificity of complementary base pairing also allows thousands of hybridization to be carried out simultaneously in the same experiment on a DNA chip (also called a DNA array).

The polymer arrays of the embodiment of the invention could be a DNA array (collections of DNA probes on a shared base) comprising a dense grid of spots (often called elements or pads) arranged on a miniature support. Each spot could represent a different gene.

The probe in a DNA chip is usually hybridized with a complex RNA or cDNA target generated by making labeled DNA copies of a complex mixture of RNA molecules derived from a particular cell type (source). The composition of such a target reflects the level of individual RNA molecules in the source. The intensities of the signals from the DNA spots of the DNA chip after hybridization between the probe and the target represent the relative expression levels of the genes of the source.

The DNA chip could be used for differential gene expression between samples (e.g., healthy tissue versus diseased tissue) to search for various specific genes (e.g., connected with an infectious agent) or in gene polymorphism and expression analysis. Particularly, the DNA chip could be used to investigate expression of various genes connected with various diseases in order to find causes of these diseases and to enable accurate treatments.

Using an embodiment of the polymer array of the invention, one could find a specific segment of a nucleic acid of a gene, i.e., find a site with a particular order of bases in the examined gene. This detection could be performed by using a diagnostic oligonucleotide made up of short synthetically assembled single-chained complementary oligonucleotide—a chain of bases organized in a mirror order to which the specific segment of the nucleic acid would attach (hybridize) via A-T or G-C bonds.

The practice of the embodiments of the invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, detection of hybridization using a label. Specific illustrations of suitable techniques can be had by reference to the example herein below. However, other equivalent conventional procedures can, of course, also be used.

As used in the specification and claims, the singular forms "a", "an" and "the" include plural references unless the context clearly dictates otherwise. For example, the term "an array" may include a plurality of arrays unless the context clearly dictates otherwise.

An "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the sample spots on the array. A macroarray generally contains sample spot sizes of about 300 microns or larger and can be easily imaged by gel and blot scanners. A microarray would generally contain spot sizes of less than 300 microns.

"Solid support," "support," and "substrate" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "probe" refers to the diagnostic oligonucleotide, which is typically a fluorescently labeled DNA or RNA.

The term "target" refers to a molecule attached to the substrate of the array, which is typically cDNA or pre-synthesized oligonucleotide deposited on the array. The oligonucleotide targets require only the sequence information of genes, and thereby can exploit the genome sequences of an organism. In cDNA arrays, there could be cross-hybridization due to sequence homologies among members of a gene family. Oligonucleotide arrays can be specifically designed to differentiate between highly homologous members of a gene family as well as spliced forms of the same gene (exon-specific). Oligonucleotide arrays of the embodiment of this invention could also be designed to allow detection of mutations and single nucleotide polymorphism.

The terms "die," "polymer array chip," "DNA array," "array chip," "DNA array chip," "biochip" or "chip" are used interchangeably and refer to a collection of a large number of targets arranged on a shared substrate which could be a portion of a silicon wafer, a nylon strip or a glass slide.

The term "molecule" generally refers to a macromolecule or polymer as described herein. However, arrays comprising single molecules, as opposed to macromolecules or polymers, are also within the scope of the embodiments of the invention.

"Predefined region" or "spot" or "pad" refers to a localized area on a solid support which is, was, or is intended to be used for formation of a selected molecule and is otherwise referred to herein in the alternative as a "selected" region. The predefined region may have any convenient shape, e.g., circular, rectangular, elliptical, wedge-shaped, etc. For the sake of brevity herein, "predefined regions" are sometimes referred to simply as "regions" or "spots." In some embodiments, a predefined region and, therefore, the area upon which each distinct molecule is synthesized is smaller than about 1 cm$^2$ or less than 1 mm$^2$, and still more preferably less than 0.5 mm$^2$. In most preferred embodiments the regions have an area less than about 10,000 $\mu$m$^2$ or, more preferably, less than 100 $\mu$m$^2$. Additionally, multiple copies of the polymer will typically be synthesized within any preselected region. The number of copies can be in the thousands to the millions. More preferably, a die of a wafer contains at least 400 spots in, for example, an at least 20×20 matrix. Even more preferably, the die contains at least 2048 spots in, for example, an at least 64×32 matrix, and still more preferably, the die contains at least 204,800 spots in, for example, an at least 640×320 array.

A spot could contain an electrode to generate an electrochemical reagent, a synthesis electrode to synthesize a polymer and a confinement electrode to confine the generated electrochemical reagent. The electrode to generate the electrochemical reagent could be of any shape, including, for example, circular, flat disk shaped and hemisphere shaped.

The electrode to generate an electrochemical reagent, the synthesis electrode or the confinement electrode that may be used in embodiments of the invention may be composed of, but are not limited to, metals such as iridium and/or platinum, and other metals, such as, palladium, gold, silver, copper, mercury, nickel, zinc, titanium, tungsten, aluminum, as well as alloys of various metals, and other conducting materials, such as, carbon, including glassy carbon, reticulated vitreous carbon, basal plane graphite, edge plane graphite and graphite. Doped oxides such as indium tin oxide, and semiconductors such as silicon oxide and gallium arsenide are also contemplated. Additionally, the electrodes may be composed of conducting polymers, metal doped polymers, conducting ceramics and conducting clays. Among the metals, platinum and palladium are especially preferred because of the advantageous properties associated with their ability to absorb hydrogen, i.e., their ability to be "preloaded" with hydrogen before being used in the methods of the invention.

The electrode(s) may be connected to an electric source in any known manner. Preferred ways of connecting the electrodes to the electric source include CMOS (complementary metal oxide semiconductor) switching circuitry, radio and microwave frequency addressable switches, light addressable switches, direct connection from an electrode to a bond pad on the perimeter of a semiconductor chip, and combinations thereof. CMOS switching circuitry involves the connection of each of the electrodes to a CMOS transistor switch. The switch could be accessed by sending an electronic address signal down a common bus to SRAM (static random access memory) circuitry associated with each electrode. When the switch is "on", the electrode is connected to an electric source. Radio and microwave frequency addressable switches involve the electrodes being switched by a RF or microwave signal. This allows the switches to be thrown both with and/or without using switching logic. The switches can be tuned to receive a particular frequency or modulation frequency and switch without switching logic. Light addressable switches are switched by light. In this method, the electrodes can also be switched with and without switching logic. The light signal can be spatially localized to afford switching without switching logic. This could be accomplished, for example, by scanning a laser beam over the electrode array; the electrode being switched each time the laser illuminates it.

In some aspects, a predefined region can be achieved by physically separating the regions (i.e., beads, resins, gels, etc.) into wells, trays, etc.

A "protecting group" is a moiety which is bound to a molecule and designed to block one reactive site in a molecule, but may be spatially removed upon selective exposure to an activator or a deprotecting reagent. Several examples of protecting groups are known in the literature. The proper selection of protecting group (also known as protective group) for a particular synthesis would be governed by the overall methods employed in the synthesis. Activators include, for example, electromagnetic radiation. ion beams, electric fields, magnetic fields, electron beams, x-ray, and the like. A deprotecting reagent could include, for example, an acid, a base or a free radical.

Protective groups are materials that bind to a monomer, a linker molecule or a pre-formed molecule to protect a reactive functionality on the monomer, linker molecule or pre-formed molecule, which may be removed upon selective exposure to an activator, such as an electrochemically generated reagent. Protective groups that may be used in accordance with an embodiment of the invention preferably include all acid and base labile protecting groups. For example, peptide amine groups are preferably protected by t-butyloxycarbonyl (BOC) or benzyloxycarbonyl (CBZ), both of which are acid labile, or by 9-fluorenylmethoxycarbonyl (FMOC), which is base labile. Additionally, hydroxyl groups on phosphoramidites may be protected by dimethoxytrityl (DMT), which is acid labile. Exocyclic amine groups on nucleosides, in particular on phosphoramidites, are preferably protected by dimethylformamidine on the adenosine and guanosine bases, and isobutyryl on the cytidine bases, both of which are base labile protecting groups. This protection strategy is known as fast oligonucleotide deprotection (FOD). Phosphoramidites protected in this manner are known as FOD phosphoramidites.

Any unreacted deprotected chemical functional groups may be capped at any point during a synthesis reaction to avoid or to prevent further bonding at such molecule. Capping groups "cap" deprotected functional groups by, for example, binding with the unreacted amino functions to form amides. Capping agents suitable for use in an embodiment of the invention include: acetic anhydride, n-acetylimidizole, isopropenyl formate, fluorescamine, 3-nitrophthalic anhydride and 3-sulfoproponic anhydride. Of these, acetic anhydride and n-acetylimidizole are preferred.

Additional protecting groups that may be used in accordance with an embodiment of the invention include acid labile groups for protecting amino moieties: tertbutyloxycarbonyl,-tert-amyloxycarbonyl, adamantyloxycarbonyl, 1-methylcyclobutyloxycarbonyl, 2-(p-biphenyl)propyl(2) oxycarbonyl, 2-(p-phenylazophenylyl)propyl(2)oxycarbonyl, .alpha., .alpha.-dimethyl-3,5-dimethyloxybenzyloxycarbonyl, 2-phenylpropyl(2)oxycarbonyl, 4-methyloxybenzyloxycarbonyl, benzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9-fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio)carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid labile groups for protecting carboxylic acids: tert-butyl ester; acid labile groups for protecting hydroxyl groups: dimethyltrityl; and basic labile groups for protecting phosphotriester groups: cyanoethyl.

The term "electrochemical" refers to an interaction or interconversion of electric and chemical phenomena.

An "electrochemical reagent" refers to a chemical generated at a selected electrode by applying a sufficient electrical potential to the selected electrode and is capable of electrochemically removing a protecting group from a chemical functional group. The chemical group would generally be attached to a molecule. Removal of a protecting group, or "deprotection," in accordance with the invention, preferably occurs at a particular portion of a molecule when a chemical reagent generated by the electrode acts to deprotect or remove, for example, an acid or base labile protecting group from the molecule. This electrochemical deprotection reaction may be direct, or may involve one or more intermediate chemical reactions that are ultimately driven or controlled by the imposition of sufficient electrical potential at a selected electrode.

Electrochemical reagents that can be generated electrochemically at an electrode fall into two broad classes: oxidants and reductants. Oxidants that can be generated electrochemically, for example, include iodine, iodate, periodic acid, hydrogen peroxide, hypochlorite, metavanadate, bromate, dichromate, cerium (IV), and permanganate ions. Reductants that can be generated electrochemically, for example, include chromium (II), ferrocyanide, thiols, thiosulfate, titanium (III), arsenic (III) and iron (II) ions. The miscellaneous reagents include bromine, chloride, protons and hydroxyl ions. Among the foregoing reagents, protons, hydroxyl, iodine, bromine, chlorine and thiol ions are preferred.

The generation of and electrochemical reagent of a desired type of chemical species requires that the electric potential of the electrode that generates the electrochemical reagent have a certain value, which may be achieved by specifying either the voltage or the current. There are two ways to achieve the desired potential at this electrode: either the voltage may be specified at a desired value or the current can be determined such that it is sufficient to provide the desired voltage. The range between the minimum and maximum potential values could be determined by the type of electrochemical reagent chosen to be generated.

An "activating group" refers to those groups which, when attached to a particular chemical functional group or reactive site, render that site more reactive toward covalent bond formation with a second chemical functional group or reactive site.

A "polymeric brush" ordinarily refers to polymer films comprising chains of polymers that are attached to the surface of a substrate. The polymeric brush could be a functionalized polymer films which comprise functional groups such as hydroxyl, amino, carboxyl, thiol, amide, cyanate, thiocyanate, isocyanate and isothio cyanate groups, or a combination thereof, on the polymer chains at one or more predefined regions. The polymeric brushes of the embodiment of the invention are capable of attachment or stepwise synthesis of macromolecules thereon.

A "linker" molecule refers to any of those molecules described supra and preferably should be about 4 to about 40 atoms long to provide sufficient exposure. The linker molecules may be, for example, aryl acetylene, ethylene glycol oligomers containing 2-10 monomer units, diamines, diacids, amino acids, among others, and combinations thereof. Alternatively, the linkers may be the same molecule type as that being synthesized (i.e., nascent polymers), such as polynucleotides, oligopeptides, or oligosaccharides.

The linker molecule or substrate itself and monomers used herein are provided with a functional group to which is bound a protective group. Generally, the protective group is on the distal or terminal end of a molecule. Preferably, the protective group is on the distal or terminal end of the linker molecule opposite the substrate. The protective group may be either a negative protective group (i.e., the protective group renders the linker molecules less reactive with a monomer upon exposure) or a positive protective group (i.e., the protective group renders the linker molecules more reactive with a monomer upon exposure). In the case of negative protective groups an additional step of reactivation will be required. In some embodiments, this will be done by heating.

The polymer brush or the linker molecule may be provided with a cleavable group at an intermediate position, which group can be cleaved with an electrochemically generated reagent. This group is preferably cleaved with a reagent different from the reagent(s) used to remove the protective groups. This enables removal of the various synthesized polymers or nucleic acid sequences following completion of the synthesis. The cleavable group could be acetic anhydride, n-acetylimidizole, isopropenyl formate, fluorescamine, 3-nitrophthalic anhydride and 3-sulfoproponic anhydride. Of these, acetic anhydride and n-acetylimidizole are preferred.

The polymer brush or the linker molecule could be of sufficient length to permit polymers on a completed substrate to interact freely with binding entities (monomers, for example) exposed to the substrate. The polymer brush or the linker molecule, when used, could preferably be long enough to provide sufficient exposure of the functional groups to the binding entity. The linker molecules may include, for example, aryl acetylene, ethylene glycol oligomers containing from 2 to 20 monomer units, diamines, diacids, amino acids, and combinations thereof. Other linker molecules may be used in accordance with the different embodiments of the present invention and will be recognized by those skilled in the art in light of this disclosure. In one embodiment, derivatives of the acid labile 4,4'-dimethoxytrityl molecules with an exocyclic active ester can be used in accordance with an embodiment of the invention. More preferably, N-succinimidyl-4[bis-(4-methoxyphenyl)-chloromethyl]-benzoate is used as a cleavable linker molecule during DNA synthesis. Alternatively, other manners of cleaving can be used over the entire array at the same time, such as chemical reagents, light or heat.

A "free radical initiator" or "initiator" is a compound that can provide a free radical under certain conditions such as heat, light, or other electromagnetic radiation, which free radical can be transferred from one monomer to another and thus propagate a chain of reactions through which a polymer may be formed. Several free radical initiators are known in the art, such as azo, nitroxide, and peroxide types, or those comprising multi-component systems.

"Living free radical polymerization" is defined as a living polymerization process wherein chain initiation and chain propagation occur without significant chain termination reactions. Each initiator molecule produces a growing monomer chain which continuously propagates until all the available monomer has been reacted. Living free radical polymerization differs from conventional free radical polymerization where chain initiation, chain propagation and chain termination reactions occur simultaneously and polymerization continues until the initiator is consumed. Living free radical polymerization facilitates control of molecular weight and molecular weight distribution. Living free radical polymerization techniques, for example, involve reversible end capping of growing chains during polymerization. One example is atom transfer radical polymerization (ATRP).

A "radical generation site" is a site on an initiator wherein free radicals are produced in response to heat or electromagnetic radiation.

A "polymerization terminator" is a compound that prevents a polymer chain from further polymerization. These compounds may also be known as "terminators," or "capping agents" or "inhibitors." Various polymerization terminators are known in the art. In one aspect, a monomer that has no free hydroxyl groups may act as a polymerization terminator.

The term "capable of supporting polymer array synthesis" refers to any body on which polymer array synthesis can be carried out, e.g., a polymeric brush that is functionalized with functional groups such as hydroxyl, amino, carboxyl etc. These functional groups permit macromolecular synthesis by acting as "attachment points."

The monomers in a given polymer or macromolecule can be identical to or different from each other. A monomer can be a small or a large molecule, regardless of molecular weight. Furthermore, each of the monomers may be protected members which are modified after synthesis.

"Monomer" as used herein refers to those monomers that are used to a form a polymer. However, the meaning of the monomer will be clear from the context in which it is used. The monomers for forming the polymers of the embodiments of the invention, e.g., a polymeric brush or a linker molecule, have for example the general structure:

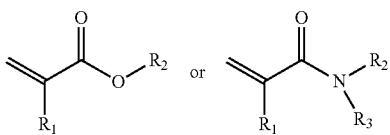

wherein $R_1$ is hydrogen or lower alkyl; $R_2$ and $R_3$ are independently hydrogen, or —Y—Z, wherein Y is lower alkyl, and Z is hydroxyl, amino, or C(O)—R, where R is hydrogen, lower alkoxy or aryloxy.

The term "alkyl" refers to those groups such as methyl, ethyl, propyl, butyl etc, which may be linear, branched or cyclic.

The term "alkoxy" refers to groups such as methoxy, ethoxy, propoxy, butoxy, etc., which may be linear, branched or cyclic.

The term "lower" as used in the context of lower alkyl or lower alkoxy refers to groups having one to six carbons.

The term "aryl" refers to an aromatic hydrocarbon ring to which is attached an alkyl group. The term "aryloxy" refers to an aromatic hydrocarbon ring to which is attached an alkoxy group. One of ordinary skill in the art would readily understand these terms.

Other monomers for preparing macromolecules of the embodiments of the invention are well-known in the art. For example, when the macromolecule is a peptide, the monomers include, but are not restricted to, for example, amino acids such as the L-amino acids, the D-amino acids, the synthetic and/or natural amino acids. When the macromolecule is a nucleic acid, or polynucleotide, the monomers include any nucleotide. When the macromolecule is a polysaccharide, the monomers can be any pentose, hexose, heptose, or their derivatives.

A "monomer addition cycle" is a cycle comprising the chemical reactions necessary to produce covalent attachment of a monomer to a nascent polymer or linker, such as to elongate the polymer with the desired chemical bond (e.g., 5'-3' phosphodiester bond, peptide bond, etc.). For example, and not to limit the invention, the following steps typically comprise a monomer addition cycle in phosphoramidite-based polynucleotide synthesis: (1) deprotection, comprising removal of the DMT group from a 5'-protected nucleoside (which may be part of a nascent polynucleotide) wherein the 5'-hydroxyl is blocked by covalent attachment of DMT, such deprotection is usually done with a suitable deprotection reagent (e.g., a protic acid: trichloroacetic acid or dichloroacetic acid), and may include physical removal (e.g., washing, such as with acetonitrile) of the removed protecting group (e.g., the cleaved dimethyltrityl group), (2) coupling, comprising reacting a phosphoramidite nucleoside(s), often activated with tetrazole, with the deprotected nucleoside, (3) optionally including capping, to truncate unreacted nucleosides from further participation in subsequent monomer addition cycles, such as by reaction with acetic anhydride and N-methylimidazole to acetylate free 5'-hydroxyl groups, and (4) oxidation, such as by iodine in tetrahydrofuran/water/pyridine, to convert the trivalent phosphite triester linkage to a pentavalent phosphite triester, which in turn can be converted to a phosphodiester via reaction with ammonium hydroxide. Thus, with respect to phosphoramidite synthesis of polynucleotides, the following reagents are typically necessary for a complete monomer addition cycle: trichloroacetic acid or dichloroacetic acid, a phosphoramidite nucleoside, an oxidizing agent, such as iodine (e.g., iodine/water/THF/pyridine), and optionally N-methylimidazole for capping.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either α-, β-, or ω-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

A "nano-material" as used herein refers to a structure, a device or a system having a dimension at the atomic, molecular or macromolecular levels, in the length scale of approximately 1-100 nanometer range. Preferably, a nano-material has properties and functions because of the size and can be manipulated and controlled on the atomic level.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

Analogs also include protected and/or modified monomers as are conventionally used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary polynucleotides (especially RNA) than their unmodified counterparts. Alternatively, deazapurines and deazapyrimidines in which one or more N atoms of the purine or pyrimidine heterocyclic ring are replaced by C atoms can also be used.

The phosphodiester linkage or "sugar-phosphate backbone" of the polynucleotide can also be substituted or modified, for instance with methyl phosphonates, O-methyl phosphates or phosphororthioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available.

Nucleotides with modified bases can also be used in the embodiments of the invention. Some examples of base modifications include 2-aminoadenine, 5-methylcytosine, 5-(propyn-1-yl)cytosine, 5-(propyn-1-yl)uracil, 5-bromouracil, 5-bromocytosine, hydroxymethylcytosine, methyluracil, hydroxymethyluracil, and dihydroxypentyluracil which can be incorporated into polynucleotides in order to modify binding affinity for complementary polynucleotides.

Groups can also be linked to various positions on the nucleoside sugar ring or on the purine or pyrimidine rings which may stabilize the duplex by electrostatic interactions with the negatively charged phosphate backbone, or through interactions in the major and minor groves. For example, adenosine and guanosine nucleotides can be substituted at the $N^2$ position with an imidazolyl propyl group, increasing duplex stability. Universal base analogues such as 3-nitropyrrole and 5-nitroindole can also be included. A variety of modified polynucleotides suitable for use in the embodiments of the invention are described in the literature.

When the macromolecule of interest is a peptide, the amino acids can be any amino acids, including $\alpha$, $\beta$, or $\omega$-amino acids. When the amino acids are $\alpha$-amino acids, either the L-optical isomer or the D-optical isomer may be used. Additionally, unnatural amino acids, for example, $\beta$-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are required for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide required for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics must take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

The term "oxidation" means losing electron to oxidize. The term "reduction" means gaining electrons to reduce. The term "redox reaction" refers to any chemical reaction which involves oxidation and reduction.

A "probe card" refers to a card whose conducting components are isolated from the environment (for example, the fluid reagents). All conducting surfaces should preferably be isolated—including the pad and point of connection between the pad and probe.

A "scribe line" is typically an "inactive" area between the active dies that provide area for separating the die (usually with a saw). Often, metrology and alignment features populate this area.

A "via interconnection" refers to a hole etched in the interlayer of a dielectric which is then filled with an electrically conductive material, preferably tungsten, to provide vertical electrical connection between stacked up interconnect metal lines that are capable of conducting electricity.

"Metal lines" within a die are interconnect lines. Unlike in the embodiments of this invention, metal interconnect lines do not typically cross the scribe line boundary to electrically connect two dies or, as in the some embodiments of this invention, a multitude of die to one or more wafer pads.

The term "wafer" means a semiconductor substrate. A wafer could be fashioned into various sizes and shapes. It could be used as a substrate for a microchip. The substrate could be overlaid or embedded with circuitry, for example, a pad, via, an interconnect or a scribe line. The circuitry of the wafer could also serve several purposes, for example, as microprocessors, memory storage, and/or communication capabilities. The circuitry can be controlled by the microprocessor on the wafer itself or controlled by a device external to the wafer.

The term "gel" means a three-dimensional porous semisolid or solid support structure that can spatially immobilize a polymer such as a sequence of oligonucleotides or a protein in three dimensions. For example, the gel could be a colloid in which the disperse phase is combined with the dispersion medium to produce a semisolid material, such as a jelly. The gel could be a hydrogel, which is a network of polymer chains that are water-insoluble, sometimes found as a colloidal gel in which water is the dispersion medium. Hydrogels are superabsorbent (they can contain over 99% water) natural or synthetic polymers. Hydrogels possess also a degree of flexibility very similar to natural tissue, due to their significant water content. The gel could also be silica-containing gel.

The embodiments of the invention are directed to:

(1) Novel application of gel-based biochips for electrochemical synthesis and electrical detection of polymers.

(2) Novel structure to enable electrochemical synthesis and electrical detection containing two measurement electrodes with the gap between them that is filled with gel and chemical probes (also referred to herein as short polymers/seeds) such as oligomers, DNA or RNA, single stranded DNA or RNA, partially double stranded DNA or RNA, proteins etc., third electrode to generate electrochemical reagents (such as protons, hydroxides etc) for electrochemical synthesis of polymers and forth electrodes that is common ground.

(3) Novel method to produce biochip (DNA, Protein arrays etc) by using the following main steps:

(a) Formation of metallization layer with electrochemical synthesis electrodes.

(b) Formation of isolation with porous $SiO_2$.

(c) Formation of metallization layer with measurements electrodes and gap between them.

(d) Filling the gap (spotting, spin on etc.) with gel (for example, porous hydrogel) covalently bonded to $SiO_2$ and chemical probes (short polymers/seeds) covalently bonded to gel.

(e) Selective electrochemical synthesis of polymers from short polymer seeds by generating reactants on electrochemical synthesis electrodes.

(f) Electrical detection of bio-species by binding chemical target to chemical probe and measuring impedance or polarization change between measurement electrodes.

Some aspects of the embodiments of this invention include:

(1) Novel structure/cell for electrochemical synthesis and electrical detection containing two measurement electrodes, synthesis electrode, common electrode, gel in gap (between two measurement electrodes) covalently bonded to porous interlevel dielectric (which is an isolation layer that covers the synthesis electrode) and chemical probes covalently bonded to gel.

(2) Novel method of electrochemical synthesis of polymers by extending short polymers/seeds covalently bonded to gel and electrical detection of target polymers bound to chemical probe by using impedance or polarization change.

Some of the technical advantages of the embodiments of this invention are:

1. Sensitivity—3D porous gel with chemical probes will allow to increase number of chemical probes per unit volume versus planar (2D) surfaces by several orders of magnitude due to larger surface area of gels. The signal (impedance or polarization change) produced due to binding events of chemical probe with target will be larger due to larger number of binding events.

2. Scalability—Use of porous 3D gels will allow to scale down the size of the devices vs devices using planar surface due to larger number of binding events available in 3D gel-based devices.

3. Stability—gel is covalently bonded to porous SiO2 and chemical probes are covalently bonded to gel increasing system stability.

4. Cost, Simplicity and Flexibility—electrochemical synthesis (allow synthesis of customized biochips) and on-chip label free electrical detection will decrease the cost and simplify the process.

5. Enable Hand held diagnostic devices—use of electrical detection will enable on chip detection which eliminates the need for stand alone optical scanner.

6. Enable Moore's law down to single molecular sensitivity. Decreasing the gel volume trapped between electrodes will result in single DNA (protein) capture and change in charge on the order of tenths of fC which can be measured.

7. Enable protein chip fabrication in gel to study the full extent of enzymatic functional activities. Complex cellular functions are carried out largely through the intricate and subtle interactions of proteins—protein—protein, protein—RNA, protein-DNA, and protein-cofactor (a small molecule essential for some proteins to carry out their function). In the theatre that is the biological cell, proteins are the main actors, and DNA is the script. A clear and quantitative view of how many actor proteins are on the stage at any given moment is crucial for understanding cellular function. Protein gel-based chips can provide us with that view. This is a significant step forward from current protein chips containing antibodies or receptor-binding domains, because simple binding is only one of the many functions proteins can have, hence these chips have limited potential.

A number of peptide- and protein-based gels have been discovered and developed over the last decade and disclosed in references in Table 1, which are incorporated herein by reference.

Table 1: References disclosing peptide- and protein-based gels.

1. Kiyonaka, S. et al. *Nature Mater.* 3, 58-64 (2004).
2. Zhang, S., Holmes, T., Lockshin, C. & Rich, A. *Proc. Natl Acad. Sci. USA* 90, 3334-3338 (1993).
3. Aggeli, A. et al. *Nature* 386, 259-262 (1997).
4. Petka, W. A., Harden, J. L., McGrath, K. P., Wirtz, D. & Tirrell, D. A. *Science* 281, 389-392 (1998).
5. Lee, J., Macosko, C. W. & Urry, D. W. *Biomacromolecules* 2, 170-179 (2001).
6. Hartgerink, J. D., Beniash, E. & Stupp, S. I. *Science* 294, 1684-1688 (2001).
7. Nowak, A. P. et al. *Nature* 417, 424-428 (2002).
8. Schneider, J. P. et al. *J. Am. Chem. Soc.* 124, 15030-15037 (2002).
9. Jin, H. J. & Kaplan, D. L. *Nature* 424, 1057-1061 (2003).
10. Zhang, S. *Nature Biotech.* 21, 1171-1178 (2003).

Figure 2:
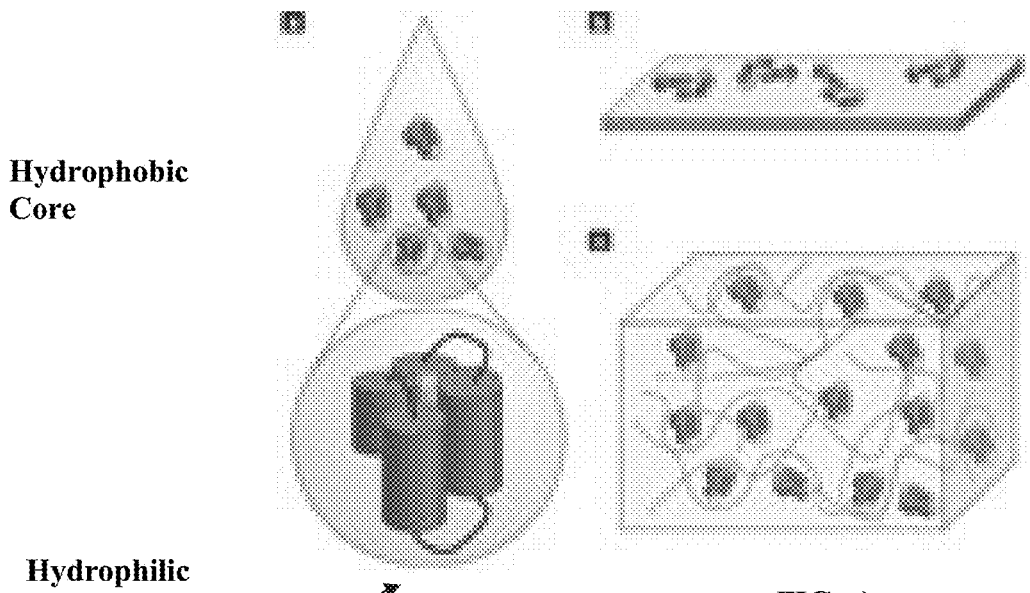
FIGS. 2(a), 2(b) and 2(c) show proteins in gels.

The gels of the embodiments of the invention form well-ordered nanofibre scaffolds with high water content ranging between 0.1-1%. This material has a high affinity towards water molecules, and thus the ability to form a gel at very low concentrations (in the range of 0.1% or 1 mg per ml), creating a dense network of nanofibres. Within this network, water molecules can easily penetrate and dwell in the hydrophilic cavities as shown in FIG. 2, which creates a habitable environment where proteins can carry out their normal functions, such as catalysis, for instance. These nanofibre scaffolds have been used for three-dimensional cell cultures, for controlled release of drugs, and other uses—but until now not for protein chips. Their range of applications will certainly expand in the coming years as more people become aware of their potential. The thing that all these different gels have in common is an extraordinary capability to trap water.

FIG. 2 shows proteins in gels. (a) When proteins are in an aqueous solution, they can fold properly, with their hydrophobic core (the inner cylinder) tucked up inside and their hydrophilic shell (the outer cylinders) exposed. (b) When proteins are left to dry or if they encounter a hydrophobic surface or solvent, they lose their folded structure and turn themselves inside out. (c) When proteins are embedded in a gel scaffold made of nanofibres, the environment that surrounds them is nearly 99% water. Thus, the proteins can fold properly and thus carry out their full biological functions.

The gel-based biochips of the embodiments of the invention have a number of advantages. First, the proteins can fold properly and thus carry out their full biological functions. In addition, the microchips could be manufactured by photoinitiated copolymerization of gel components and immobilized molecules (DNA, proteins, and ligands). This ensures an even distribution of the immobilized probe throughout the microchip gel element with a high yield (about 50% for oligonucleotides). In one embodiment, the use of methacrylamide as a main component of the polymerization mixture would result in a substantial increase of gel porosity without affecting its mechanical properties and stability, thus allowing one to work with the DNA fragments of up to 500 nt in length, as well as with quite large protein molecules. The generic microchips containing a complete set of possible hexanucleotides could be used to reveal the DNA motifs binding with different proteins and to study the DNA-protein interactions. The biochips of the embodiments of the invention could used for identification of the tuberculosis pathogen and its antibiotic-resistant forms; of orthopoxviruses, including the smallpox virus; of the anthrax pathogen; and chromosomal rearrangements in leukemia patients. The protein microchips could be used in proteomics. Bacterial and yeast cells could also be immobilized in the gel, maintaining their viability, thereby opening creating biosensors on the basis of microchips.

The embodiments of the invention can be used to carry out the electrochemical syntheses of polymers such as DNA and peptides according to any of a variety of approaches known to person skilled in the art. For example, any of a variety of reduction/oxidation (redox) reactions may be employed to electrochemically control the localization and pH of a solution on Si-based electrodes to enable the attachment and elongation of polymers. In such methods, the electrical current drives the oxidation of an appropriate molecule at the anode(s) and the reduction of another molecule at the cathode(s) to control the kinetics and stoichiometry of acid-catalyzed organic syntheses on a Si-based circuit. Such methods can also be used to generate high pH (basic) solutions, and to drive any other electrochemical redox reactions known to one skilled in the art that may or may not result in pH changes (e.g., can also be used to generate reactive free radicals).

In one embodiment of the invention, the electrochemically generated acid solutions also can enable coupling reactions between the monomers and acceptors that are widely used to synthesize polymers such as nucleic acid oligomers and peptides.

Another embodiment of the invention is electrochemical detection using the array chip. For example, a variety of published methods describe DNA binding detection. Typically these methods employ measurements of current flow across a DNA monolayer tethered to a circuit on a silicon substrate. Current flow properties proportionately change when the DNA monolayers are bound by an appropriate redox molecule-tagged test DNA or untagged DNA that is co-added with a redox-active molecule that specifically binds double stranded DNA. Enzyme amplification methods can also be incorporated into such assays in order to enhance the electrochemical signal generated by binding events. Note that these methods can also be adapted by one skilled in the art to measure the binding between other molecular species such as between two proteins or a protein and a small molecule.

The embodiments of the invention cover arrays used for research (typically high density with many different probes) as well as diagnostics (typically low density because one is generally looking for only a few specific analytes in a sample for diagnostics). The array chip of an embodiment of the invention could be uses for screening large numbers of polymers for biological activity, for example. To screen for biological activity, for example, in the field of pharmaceutical drug discovery, the substrate is exposed to one or more receptors such as antibodies, whole cells, receptors on vesicles, lipids, or any one of a variety of other receptors. The probes are preferably labeled with, for example, an electrochemical marker, an electro-chemiluminescent marker, a chemiluminescent marker, a fluorescent marker, a radioactive marker, or a labeled antibody reactive with the probe. The position of the probe on the substrate after hybridization is detected with, for example, electrochemical, fluorescence or autoradiographic techniques.

The array chip could also be used for therapeutic materials development, i.e., for drug development and for biomaterial studies, as well as for biomedical research, analytical chemistry, high throughput compound screening, and bioprocess monitoring. An exemplary application includes applications in which various known ligands for particular receptors can be placed on the array chip and hybridization could be performed between the ligands and labeled receptors.

Yet another application of the array chip of an embodiment of this invention includes, for example, sequencing genomic DNA by the technique of sequencing by hybridization. Non-biological applications are also contemplated, and include the production of organic materials with varying levels of doping for use, for example, in semiconductor devices. Other examples of non-biological uses include anticorrosives, antifoulants, and paints.

It is specifically contemplated that the array chip and/or the methods of manufacturing the array chip of an embodiment of the invention could be used for developing new materials, particularly nano-materials for many purposes including, but not limited to corrosion resistance, battery energy storage, electroplating, low voltage phosphorescence, bone graft compatibility, resisting fouling by marine organisms, superconductivity, epitaxial lattice matching, or chemical catalysis. Materials for these or other utilities may be formed proximate to one or a plurality of the electrodes in parallel on a plurality of dies of a silicon wafer, for example. Alternatively, materials may be formed by modifying the surface of one or a plurality of electrodes on a plurality of dies by generating reagents electrochemically.

It is further contemplated that an array chip of the embodiments of the invention could be used to develop screening methods for testing materials. That is, reagents electrochemically generated by an electrode on a die could be used to test the physical and chemical properties of materials proximate to the electrode. For example, the array chip could be used for testing corrosion resistance, electroplating efficiency, chemical kinetics, superconductivity, electro-chemiluminescence and catalyst lifetimes.

The advantageous characteristics of some of the embodiments of the invention are illustrated in the following examples, which are intended to be merely exemplary of the invention.

Figure 3:
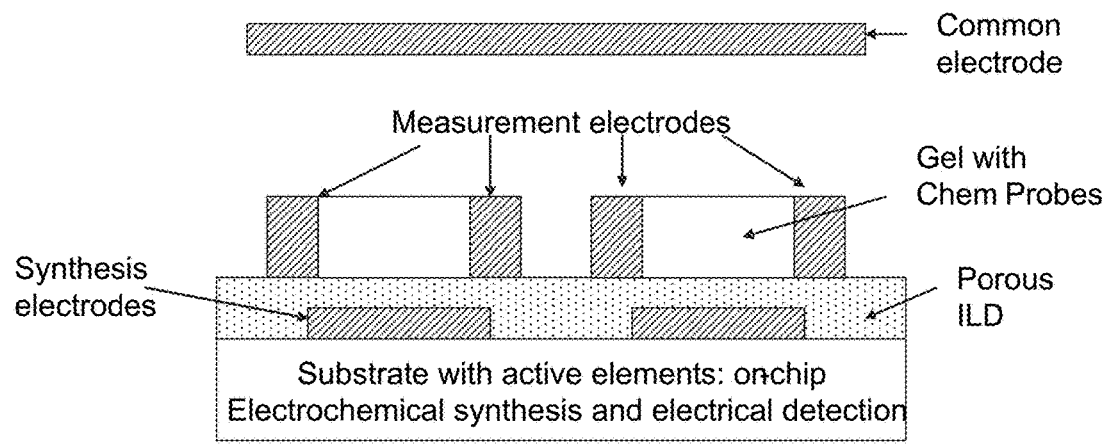
FIG. 3 shows a cross sectional view of a biochip.

The array chips of the embodiments of the invention are preferably silicon biochips built by using silicon process technology and SRAM like architecture with circuitries including electrode arrays, decoders, serial-peripheral interface, on chip amplification, for example. An embodiment of the biochip of the invention for electrochemical synthesis and electrical detection is shown in FIG. 3. The novel structure/cell of the biochip comprises at least two measurement electrodes, one or more synthesis electrodes, one or more common electrodes (ground), gel in the gap between the two measurement electrodes covalently bonded to porous interlevel dielectric (ILD) such as $SiO_2$, and chemical probes (oligomers, proteins etc.) covalently bonded to the gel. The chemical probes could be within the gel or the surface of the gel.

Another embodiment includes gel containing water and protein. Another embodiment of the present invention includes gel containing metallic particles to provide conductivity of the gel and this conductivity will be changed when target will be bound to chemical probe thus changing the gel conductive paths. Another embodiment of the present invention could use gel with charged surface (charged surface groups, for example COOH—, $NH_2$+ etc). Charged chemical probes and targets will change the surface charge of porous gel. Another embodiment of the present invention includes tagged target molecules bound to chemical probes with conductive particles being used as a tag. Another embodiment includes the generation of catalytic current on electrodes by coupling enzyme-catalyzed reactions that generate electrical signals, or amplify existing signals, when probe/target recognition events occur on the porous gel surface.

Figure 4:
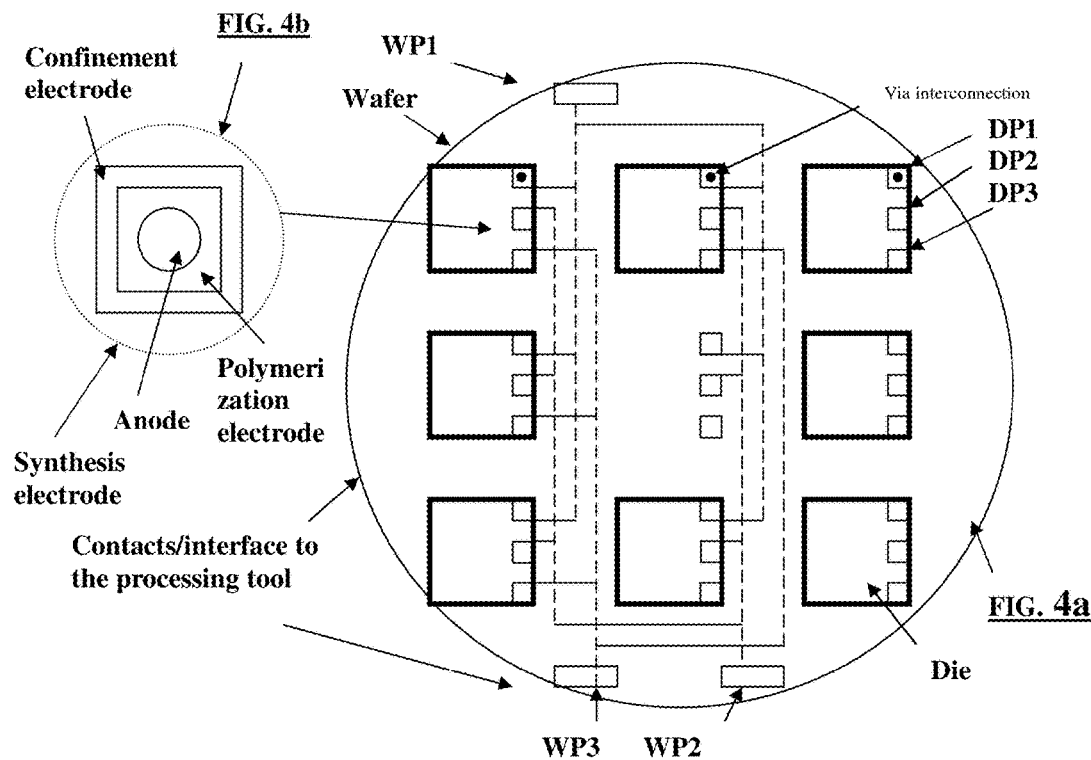
FIGS. 4(a) and 4(b) show top view of the wafer having a plurality of gel-based biochips.
FIG. 4(c) depicts an illustrative example of a probe card.
Figure 4C:

In one embodiment, a plurality of cells could be built on a wafer a shown in FIG. 4. In this case the wafer could further have interconnects and biochip pads on the wafer, wherein biochip pads of the plurality of cells are interconnected by the interconnects to carry out a chemical reaction on a plurality of synthesis electrodes of the plurality of the cells. The biochip pads are shown as DP1, DP2, DP3 and the wafer-pads are shown as WP1, WP2, WP3 in FIG. 4(a). The synthesis electrodes could include anodes to generate acid, polymerization electrodes to polymerize a polymer thereon and confinement electrodes to confine protons. These electrodes are shown in FIG. 4(b). The biochip pads are used for power, signal delivery, for example. The biochip pads could be interconnected by either using a multilevel interconnect (two or more layers) across a scribe line on the front side of the wafer as shown in FIG. 4(b) or using a via interconnect that traverses from the front side of the wafer to the backside of the wafer. The via connect could be connected to electrical contact on the backside of the wafer and further to an outside contact located outside the wafer in a processing tool such as a wafer holder. Electrochemical synthesis occurs on the synthesis electrodes when activated. The CMOS circuitry, shown here as a block diagram, decodes the input address and signal. In contract to typical silicon devices in which power and signal is input to the CMOS circuitry through a topside wire bond pad or solder bump connection, in this technique, the connection is made through the backside via.

In other embodiments of the invention, the cell could comprise CMOS circuitry to be connected to measurements, synthesis or common electrodes. The CMOS circuitry amplifies the signal, reads and writes information on the different electrodes (i.e. functionalize the synthesis electrodes and read out biding events), besides performing other functions.

The silicon biochip for wafer level polymer synthesis could be fabricated by the following steps, for example, which are described with reference with FIG. 3:

(1) Formation of a metallization layer of a noble metal such Pt, Ru, Ir etc, Al, refractory metals such as Ti, Nb, Mo, Ta etc. for the electrochemical synthesis electrodes.

(2) Formation of the isolation layer with porous $SiO_2$.

(3) Formation of a metallization layer creating a gap therein to create measurements electrodes and the gap therein.

(4) Filling the gap (spotting, spin on etc) with gel covalently bonded to $SiO_2$ and chemical probes (short polymers/seeds) covalently bonded to gel. Examples of the gel can include gel formed through the supramolecular assembly in water of a small molecule (less than 700 daltons) with a hybrid structure. At one end, this molecule contains a polar moiety (a sugar) that interacts favorably with water—that is, it is hydrophilic—and at the other end, linked through an amino acetate unit for example, are two non-polar moieties such two methylcyclohexyl rings, forming a hydrophobic group.

(5) Selective electrochemical synthesis of polymers on short polymer seeds such as oligomers by generating reagents on electrochemical synthesis electrodes.

(6) During or the manufacture of the biochip, it is possible to undertake electrical detection of bio-species by binding chemical target to chemical probe and measuring impedance or polarization change between measurement electrodes.

As explained by A. Yu. Rubina, et al. in "Hydrogel-Based Protein Microchips: Manufacturing, Properties, and Applications" *BioTechniques* 34: 1008-1022 (May 2003) (incorporated herein by reference), a simple and reproducible procedure for large-scale manufacturing of biochips with an immobilized microarray of gel elements with different short polymers/seeds such as oligomers, partially a double stranded DNA, DNA or RNA fragments, protein and ligands could be as follows. The gel could be covalently bonded to $SiO_2$ and chemical probes covalently bonded on the surface of the pores in the gel. The manufacturing comprises of three steps: (a) modification of proteins with polymerization monomer; (b) the robotic application of drops of the polymerization mixture with a pin or jet printer on a gap between the measurement electrodes shown in FIG. 3; and (c) the photo-induced copolymerization of modified proteins with gel monomer. The third step is photo-induced copolymerization of acrylamide-based gel monomers with proteins, oligonucleotides, DNA, or low-molecular ligands modified by the introduction of methacrylic groups in miniature drops. The three steps are explained below in further details.

Incorporation of methacrylic groups into short polymers/seeds:

In one example, the short polymer could be a protein. The protein could be, for example, insulin, antibodies (human immunoglobulin G, polyclonal antibodies to horseradish peroxidase (HRP), monoclonal antibodies to prostrate-specific antigen), L-sapartate aninotransferase, bovine serum albumin (BSA), HRP, Protein A, β-Lactoglobulin, and Barnase conditioned with 1-5 methacrylic groups. For example, protein solution (100 microliter at 20 micromole) in 0.01 M borate buffer, pH 9.3, could be mixed with 20 microliter of a o.110 mM solution of N-hydroxysuccinimide ester of 6-methacrylaminohexanoic acid in dimethyl formamide (DMF), and the mixture could be stirred from 0.5 to 2 hours at room temperature. The protein:modifier molar ration could be varied from 1:1 to 1:100. The modified proteins could be purified in a Micro Bio-Spin column with Sephadex G-25 or used for copolymerization in the reaction mixture without purification. The number of methacrylic groups introduced into the proteins with molecular masses up to 60 kDa could be determined by mass spectroscopy.

Fabrication of Biochip:

(a) Filling the Gap with Gel:

In one example, solution of copolymerization mixture containing, for example, 3.7% methacrylamide (w/v), 0.3% N,N'-methyl-enebisacrylamide (w/v), 50% glycerol (v/v), and modified protein (0.5 mg/ml in 0.01 M phosphate buffer saline (PBS) containing 150 mM NaCl, pH 7.2) could be transferred to the gap between the measurement electrodes by spotting in the gap by a robot pin or piezoelectric head. Then the polymerization of the gel could be carried out under UV light with a maximal wavelength of 35 nm, irradiation intensity at 0.06 microWatt/cm$^2$, using for example Sylvania GTE lamp, F15T8/350 BL, 15 W power, 8 cm distance from the lamp, for 20 min at 20° C. in dry nitrogen. After polymerization, the biochip could be washed with 50 microliter 0.01 M PBS, pH 7.2, containing 0.1% Tween® 20 (PBST) and stored in 0.01 M PBS containing 20% to 40% glycerol at 10° C.

(b) Electrochemical Synthesis:

The electrochemical synthesis of polymers in the embodiments of the invention is performed by extending the short polymers/seeds covalently bonded to gel. Synthesis of polymers (DNAs etc) on the electrodes is performed by using electrochemically generated reagents (acids, bases, radicals etc) that reacts with molecules on the electrode surface to polymerize, protect, and/or deprotect polymer subunits using acid-catalyzed polymer synthesis method.

Figure 5:
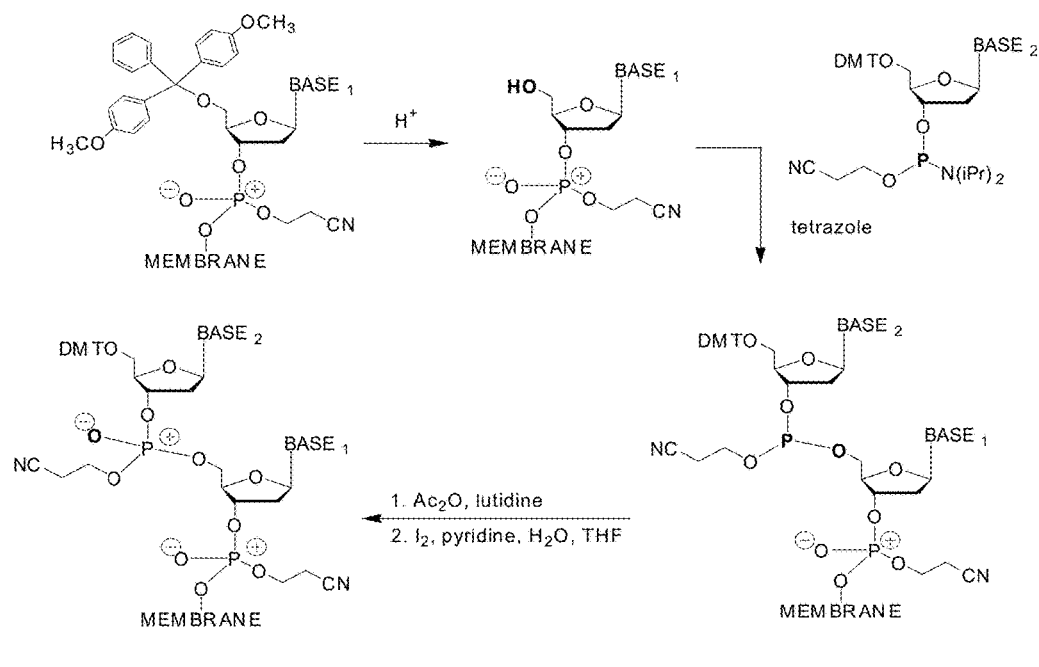
FIG. 5 shows an acid-catalyzed polymer synthesis scheme of an embodiment of the invention.

FIG. 5 shows an exemplary scheme for the synthesis of polymers on the individually addressable electrodes on the wafer by generating acid on the electrodes through an electrochemical reaction to polymerize, protect, and/or deprotect polymer subunits using an acid-catalyzed polymer synthesis scheme. The synthesis scheme of FIG. 5 is also applicable for acid catalyzed polymer synthesis for the manufacture of nucleic acids such as DNA. FIG. 5 shows that by applying a voltage to a metal electrode, protons are generated in a redox buffer. The protons in turn catalyze the synthesis of DNA one base pair at a time according to the synthesis scheme of FIG. 5. While performing of the parallel synthesis of a material it would be preferable to apply a specific potential to confinement electrodes surrounding the synthesis electrodes to effectively confine protons to the synthesis electrodes by an electrochemical means and to prevent diffusion-controlled spreading of protons to neighboring synthesis electrodes Another embodiment includes parallel synthesis of polymers such as DNA on the working or synthesis electrodes of different dies by connecting to the pads on the wafer using a sealed probe card.

Figure 6:
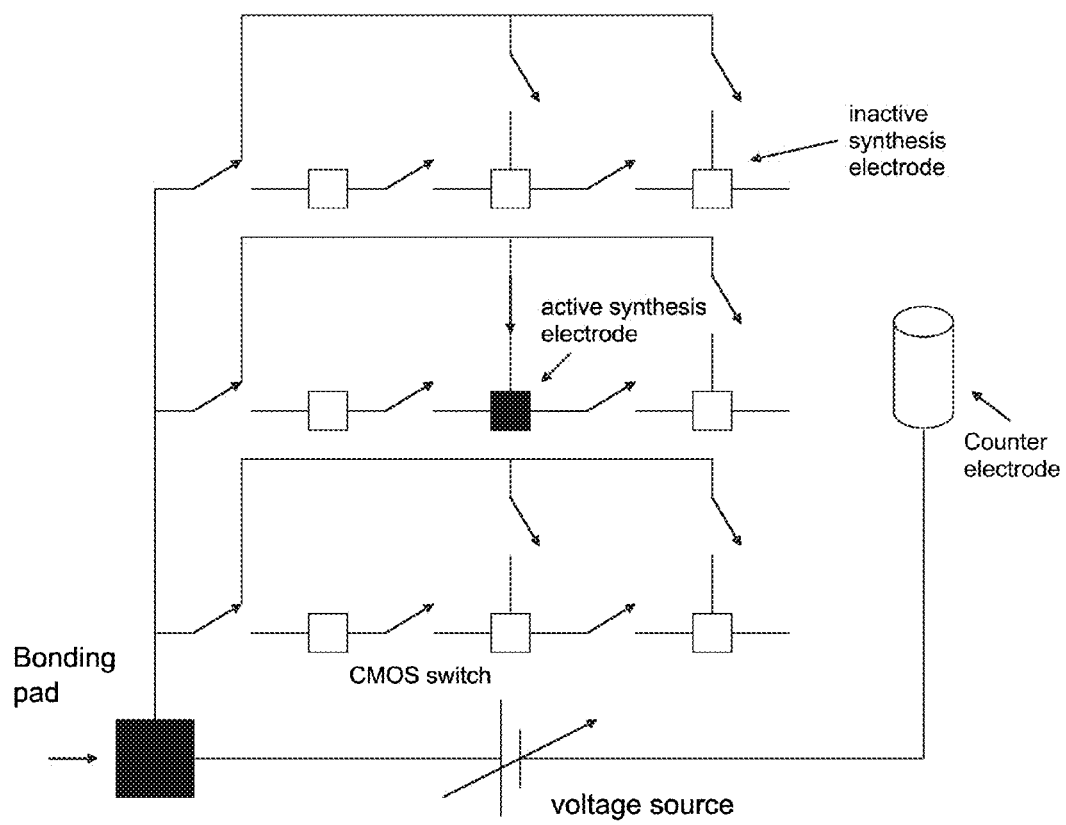
FIG. 6 shows a CMOS switching scheme for individually addressable electrodes.

Parallel synthesis of a material such as polymers (e.g., DNA) or a nano-material on the synthesis electrodes of different spots of a biochip or of different biochips on the wafer can be accomplished by using electrochemically generated reagents (acids, bases, radicals, etc.) that reacts with a molecule on the surface of the synthesis electrode. FIG. 6 shows CMOS switching scheme for individually addressing different synthesis electrodes on the wafer. In FIG. 6, each biochip pad on the biochip branches into a large array of synthesis electrodes. These electrodes are exposed to the electrolyte and can be modified with polymer (e.g., DNA). CMOS switches ensure that a given electrode (or an entire column, or an entire row) can be modified one base pair at a time. Voltage source and counter electrode (plating tool) are shown to complete the electrical circuit.

Figure 7:
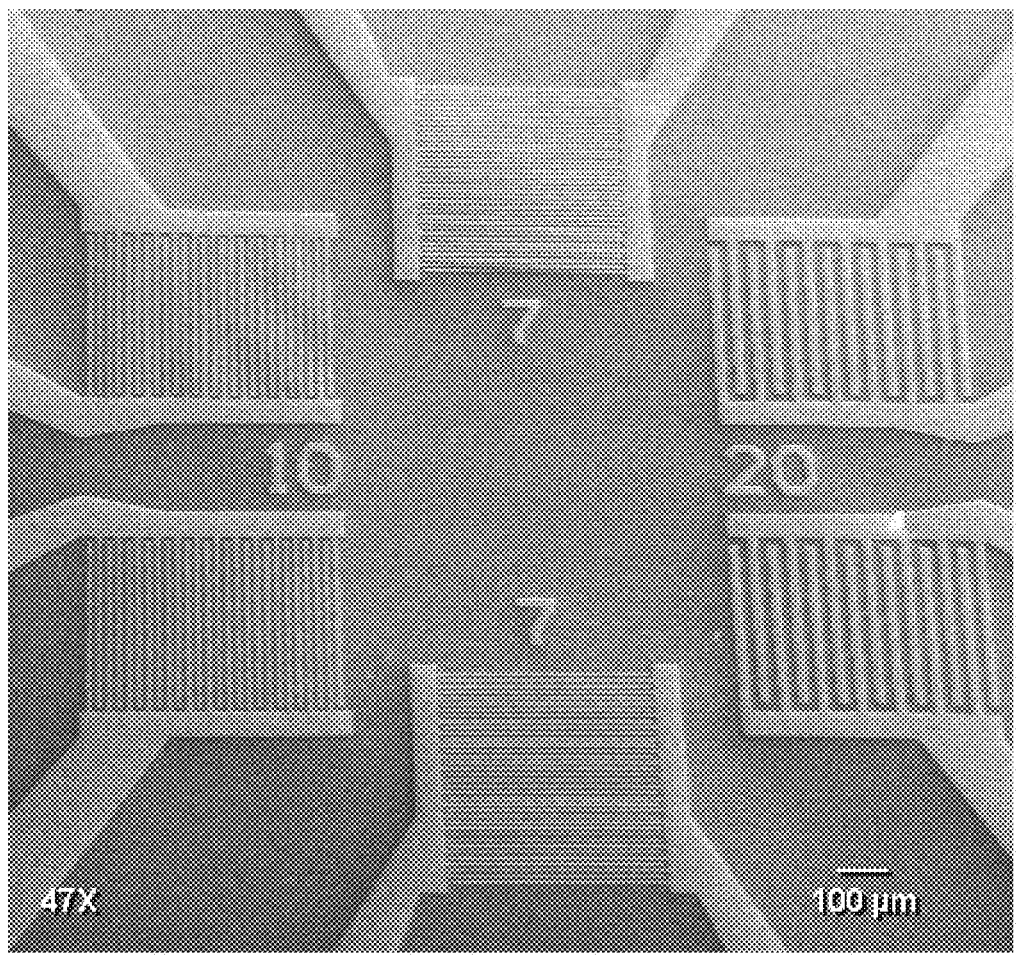
FIG. 7 shows capacitance measurements of electrodes.

Electrical Detection:

Other embodiments of the invention include electrical detection of target polymers bound to chemical probe on the surface of porous gel by using impedance or polarization change. The generated charge for a single-stranded DNA with 25 base pairs undergoing hybridization with a complimentary strand is about $50 \times 1.6 \times 10^{-19}$ C. The surface coverage of the DNA bound to the electrode could be estimated conservatively to be on the order of $10^{10}$ DNA molecules per cm$^2$ (while as high as $10^{12}$ cm$^{-2}$ have been reported). Thus, the surface charge on 10 micron×10 micron planar electrode without porous gel will be in the fC range while the surface charge for porous gel will be several orders of magnitude larger. If protein displaces water in the gel, it will result in effective dielectric constant change (81 for H$_2$O to 2 for polymer). Dielectric constant change will result in a capacitance change that can be measured. Binding events of molecules to the proteins can thus be detected due to change in the effective dielectric constant of composite material (water displacement by polymer molecules results in Keff change from 81 to about 2). Ability to measure fC charge due to polarization change in polymer was demonstrated. In particular, changes in the double layer capacitance of the cell with and without DNA, as well as before and after hybridization, was demonstrated (see FIG. 7). FIG. 7 shows capacitance measurements of electrodes: pure Gel C1=48–54 pF; Gel with oligonucleotide C2=57–67 pF; pure Gel+hybridization C1=75–80 pF; Gel with oligonucleotide+hybridization C2=82.5–88 pF.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A wafer comprising a plurality of biochips and interconnects, each of the plurality of biochips comprising a biochip pad, at least two measurement electrodes, a synthesis electrode, a ground electrode, a gap between the at least two measurement electrodes, a porous dielectric isolation layer that electrically isolates the measurement electrodes from the synthesis electrode, and a gel comprising a probe, wherein a plurality of the biochip pads of the plurality of the biochips are interconnected by the interconnects to carry out a chemical reaction on a plurality of the synthesis electrodes, wherein the wafer comprises a via interconnection through the wafer, and the biochip pads of the plurality of biochips are interconnected by the via interconnection.

2. The wafer of claim 1, wherein the chemical reaction is an electrochemical redox reaction.

3. The wafer of claim 1, wherein the biochip pads are interconnected to carry out the chemical reaction in parallel on the plurality of the synthesis electrodes.

4. The wafer of claim 1, wherein the synthesis electrode comprises an electrode to generate a deprotecting reagent, a polymerization electrode to polymerize a polymer thereon, and a confinement electrode adjacent to the polymerization electrode to confine a reductive molecule or an oxidative molecule.

5. The wafer of claim 4, wherein the reductive molecule comprises a proton, a free radical, or combination thereof.

6. The wafer of claim 4, wherein the oxidative molecule comprises a hydroxyl ion, a free radical, or combination thereof.

7. The wafer of claim 1, wherein the wafer comprises a wafer pad, and wherein the biochip pads of the plurality of biochips are interconnected by the via interconnect to the wafer pad.

8. The wafer of claim 1, wherein the biochip pads of the plurality of biochips are configured to be interconnected to a connection outside the wafer through the via interconnect.

9. The wafer of claim 1, wherein the biochip pads of the plurality of biochips are configured to be interconnected by a probe card.

10. The wafer of claim 1, wherein each of the plurality of biochips further comprises a complementary metal oxide semiconductor (CMOS) switch between the biochip pad and the synthesis electrode.

11. The wafer of claim 1, wherein the gel is in the gap, and the porous dielectric isolation layer is between the synthesis electrode and the gel, wherein the gap is filled with the gel.

* * * * *